United States Patent [19]
Bedi et al.

[11] Patent Number: 4,805,617
[45] Date of Patent: Feb. 21, 1989

[54] SURGICAL FASTENING SYSTEMS MADE FROM POLYMERIC MATERIALS

[75] Inventors: James J. Bedi, Cincinnati, Ohio; Donald M. Golden, Cherry Hill, N.J.; Mark T. Gaterud, Flemington, N.J.; Anthony S. Miksza, Bound Brook, N.J.; Jose C. Deniega, Readington, N.J.; Richard Smith, Cincinnati, Ohio; W. Brinton Yorks, Jr., Yardley, Pa.

[73] Assignee: Ethicon, Inc., Somerville, N.J.

[21] Appl. No.: 117,592

[22] Filed: Nov. 5, 1987

[51] Int. Cl.$^4$ ............................................. A61B 17/04
[52] U.S. Cl. .............................. 128/334 C; 128/334 R
[58] Field of Search ........................ 128/334 R, 334 C

[56] References Cited

U.S. PATENT DOCUMENTS

| | | | |
|---|---|---|---|
| 4,060,089 | 11/1977 | Noiles | 128/325 |
| 4,402,445 | 9/1983 | Green | 227/19 |
| 4,506,670 | 3/1985 | Crossley | 128/334 R |
| 4,506,671 | 3/1985 | Green | 128/334 R |
| 4,513,746 | 4/1985 | Aranyi et al. | 128/334 C |
| 4,534,350 | 8/1985 | Golden et al. | 128/334 C |
| 4,534,352 | 8/1985 | Korthoff | 128/334 C |
| 4,548,202 | 10/1985 | Duncan | 128/334 C |
| 4,589,416 | 5/1986 | Green | 128/334 C |
| 4,610,250 | 9/1986 | Green | 128/334 C |
| 4,724,839 | 2/1988 | Bedi et al. | 128/334 C |

Primary Examiner—Allen M. Ostragar
Attorney, Agent, or Firm—Paul A. Coletti

[57] ABSTRACT

An improved surgical fastener system comprising parallel rows of staples and receivers with the receivers connected to adjacent receivers by a plurality of linkages.

22 Claims, 9 Drawing Sheets

SURGICAL FASTENING SYSTEMS MADE FROM POLYMERIC MATERIALS

This is a continuation-in-part of U.S. patent application Ser. No. 839,407, filed Mar. 14, 1986.

The present invention relates to surgical fastening systems for closing wounds and more particularly to surgical fastening systems made from polymeric materials for use in closing internal wounds in humans or animals.

BACKGROUND OF THE INVENTION

For many years surgical wounds and other internal and skin wounds, have been closed using sutures and needles. In more recent times a number of skin stapling instruments have been developed. These instruments apply a series of metal staples to an external wound; that is, a skin wound, to close the wound. In many instances, such skin stapling instruments have replaced the suturing of such wounds. Also, in more recent times instruments have been developed to apply metal fasteners such as staples internally to close internal wounds during a surgical procedure. The primary advantages of the instruments which apply staples to wounds is that they greatly reduce the time required to close the wound and present minimum traumatic effects to improve healing of tissue. Both factors lead to reduced blood loss and improved patient care. Thus, these instruments have considerable medical benefits and economic benefits in surgical procedures. A major disadvantage of closing wounds with metallic staples are that very often the patient requires subsequent diagnostic procedures such as x-rays, cat scanning, and the like, and the metal staples often disrupt such diagnostic procedures. To overcome this last drawback, a number of polymeric fastening systems have been developed which use fasteners made from polymeric materials placed by a suitable instrument to close the wound. Examples of such fastening systems are more fully disclosed in U.S. Pat. Nos. 4,060,089, 4,532,927; 4,532,926; and 4,513,746.

In European patent application No. 84401937.2, Publication No. 0136949, there is disclosed a surgical fastening system made from polymeric materials which has a primary use of closing internal wounds. The system comprises a two-piece fastening member that is a staple which penetrates the tissue to be closed and a retainer or receiver which interlocks with that staple once it has penetrated the tissue to maintain the wound closed. In this patent, the retainers are connected to one another by yieldable links, that is flexible or frangible links. The links are used to maintain the receivers together to assist in loading instruments with the receivers, and it is desired that once applied to the tissue the links break so as not to restrict movement of the tissue.

While such polymeric fastening systems may be made from many different polymer materials, it is desirable that the fasteners be made from absorbable polymeric materials; that is, material that will be hydrolyzed or absorbed by human tissue. By making the fasteners of such absorbable materials, once placed and once the tissue is joined, the material is absorbed by the human body and, hence, no foreign material remains in the human body which may be disruptive and cause complications. It is important to make the fasteners of material that will have sufficient strength to maintain its integrity after it has been placed to hold the tissue together for a sufficient period of time to allow the tissue to heal before the material starts to lose its strength and be absorbed.

What we have discovered is a specific configuration of a fastening system comprising staples and receivers which not only provides for ease and loading of the instruments with the fasteners and, hence, the desired economics, but also when made from absorbable polymeric materials, has sufficient strength to maintain the desired configuration until the tissue has healed. It is a further object of the present invention to provide a configuration which will move or flex with the tissue that has been joined yet will maintain its configuration and aid in the healing or joining of the tissue. We have discovered that by joining the receivers in a two-piece absorbable polymeric system in a specific manner, not only do we get the economic benefits in manufacture and the medical benefits in reducing the time for the surgical procedure, but unexpectedly we obtain more desirable healing characteristics when using our new fastening system to join wounds.

SUMMARY OF THE PRESENT INVENTION

Instruments used in the internal fastening of wounds generally apply at least two parallel rows of staples. When the instrument is to apply fasteners of absorbable materials, it will apply at least a pair of parallel rows of staples and a pair of parallel rows of receivers. The staples each comprise a pair of legs connected at one end by a link with the free end of the legs of the staples being sharpened or otherwise adapted to penetrate the tissue. The staple is applied to the tissue by penetrating the tissue with the legs so that the linking member lies adjacent the tissue. A receiver, generally a member which has a pair of apertures spaced so that the legs will fit therethrough, is placed on the opposite side of the tissue and the apertures or openings in the receiver engage with the legs of the staple to lock the staple and receiver together and join the tissue. Hence, the instrument is carrying at least two parallel row of staples in one jaw of the instrument which is placed on one side of the tissue and at least two parallel rows of receivers in the opposite jaw o the instrument placed on the other side of the tissue to be joined. The tissue to be joined is placed between the jaws of the instrument, the jaws are brought together, and the staples fired so that the legs penetrate the tissue and engage the openings in the receivers and then the staples and receivers are released from the instrument. In our improved fastening system, the receivers are connected to at least two receivers in an adjacent row with each connection comprising a plurality of parallel linkages between the receivers. The linkages are flexible and sufficiently strong to maintain the receivers connected during both the application of the fastening system and the use of the fastening system to join and hold the tissue. In a preferred embodiment of the present invention the area between the openings of a receiver is depressed or recessed. The recesses allow for excess tissue and prevent strangulation of the tissue. This configuration produces good hemostasis while allowing blood to be supplied to the tissue to support tissue life and prevent necrosis. As previously mentioned, it is critical to the present invention that the receivers be joined or held together until the wound has healed. By insuring that the receivers are held together while the tissue is healing, improved hemostatis is obtained and prevention of wandering of the fasteners is eliminated. It is desired that there be some flexibility in the connected receivers so that if the patient moves and the tissue being joined is moved slightly, the fastening system will move or flex with the tissue and the desired hemostatis maintained. By joining a receiver to two adjacent receivers with at least three parallel linkages at each juncture, we have been able to obtain the desired flexibility in the final closure and maintain good hemostatis throughout the healing process. Furthermore, the receiver being made from absorbable materials, as it is being absorbed by the human body it tends to lose strength and unless adequately and correctly joined may break apart during the healing process which is undesirable. By joining each receiver to at least two receivers and by having each juncture at least three parallel linkages even if one, or two, or three linkages break during the healing process, there is still sufficient connection to maintain the desired hemostatis throughout the healing operation. Furthermore, even if stresses are placed on the wound sufficient to break a couple of the linkages, there are still sufficient linkages to maintain the desired configuration of the fastening system and adequate hemostatis throughout the wound healing process.

BRIEF DESCRIPTION OF THE DRAWINGS

The invention will be more fully described in conjunction with the accompanying drawings wherein:

FIGS. 23-37 illustrate yet another embodiment of the fastening system of the present invention in which the receivers are channeled to provide improved stiffness.

DETAILED DESCRIPTION OF THE DRAWINGS

Figure 1:
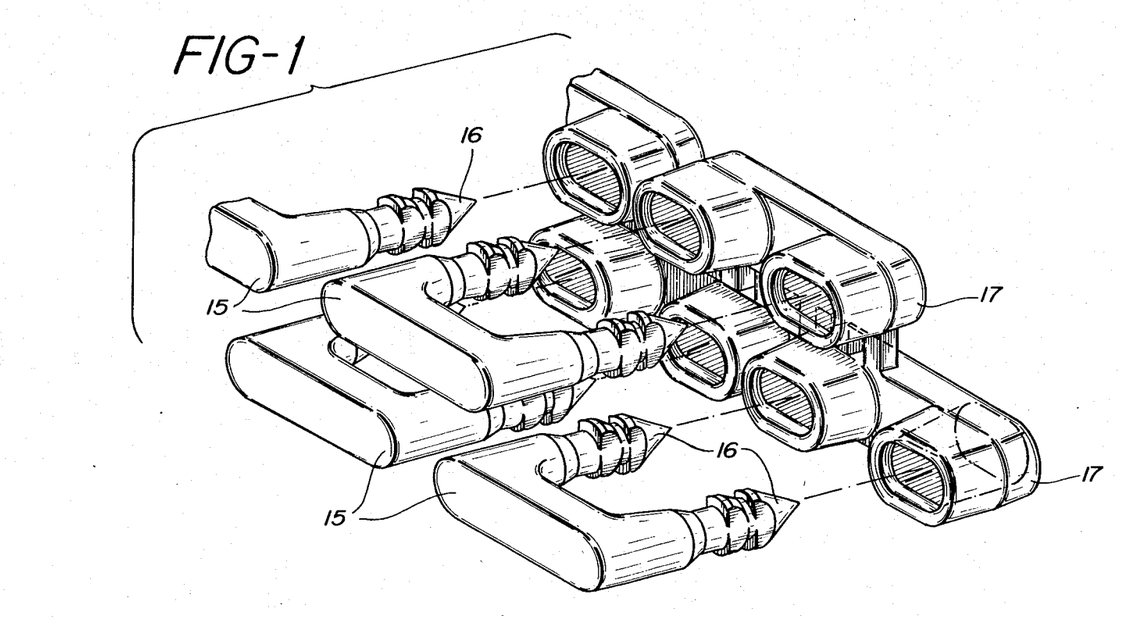
FIG. 1 is a perspective view of the fastening system of the present invention.

Referring to FIG. 1 there is shown a portion of a fastening system of the present invention in a perspective view. The fastening system comprises two parallel rows of individual staples 15. The legs 16 of the staples are designed to penetrate the tissue to be joined and lock or join therein to a plurality of receivers 17. The receivers comprise two parallel rows of individual receivers with each receiver connected to at least two adjacent receivers with each juncture comprising a plurality of parallel linkages.

Figure 2:
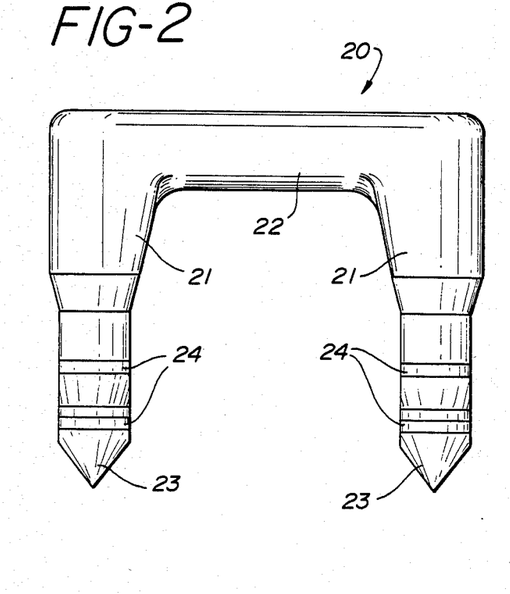
FIG. 2 is a front view of a staple member of the fastening system of the present invention.
Figure 3:
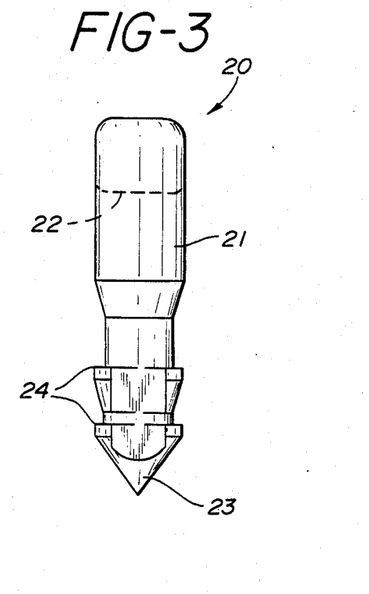
FIG. 3 is an end view of the staple shown in FIG. 2.

As more clearly shown in FIGS. 2 and 3, each staple 20 comprises a pair of legs 21. The legs are joined at one end by a suitable linkage 22. In use, the legs penetrate the tissue to be joined, and the linkage rests on the surface of one side of the tissue being joined. Each leg has a free end 23 which in this embodiment is pointed or sharpened to assist in penetrating the tissue. Also disposed along the free ends of the legs are suitable means 24 for locking the legs of the staple with the receiver. In this embodiment, there are two locking means to adjust the distance between the staple and the receiver depending on the thickness of the tissue to be joined. The locking means comprise oppositely disposed ledges which are spaced along the leg of the staple from the pointed end. As will be discussed, these ledges interlock or catch with oppositely disposed ledges in the receiver.

Figure 4:
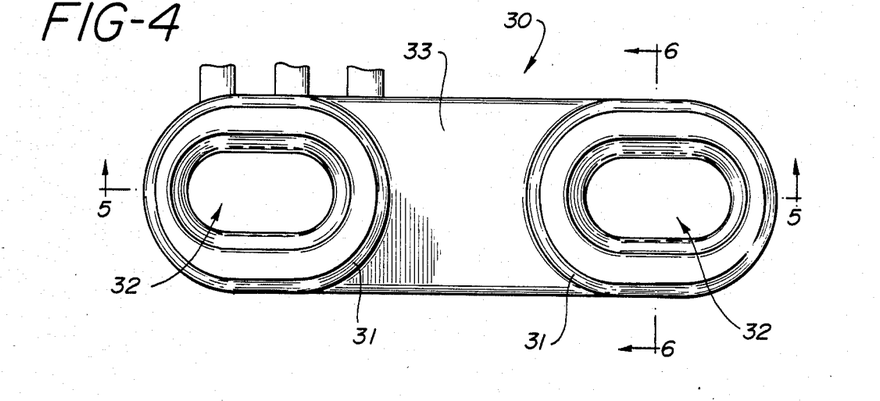
FIG. 4 is a top view of a receiver used in the fastening system of the present invention.
Figure 5:
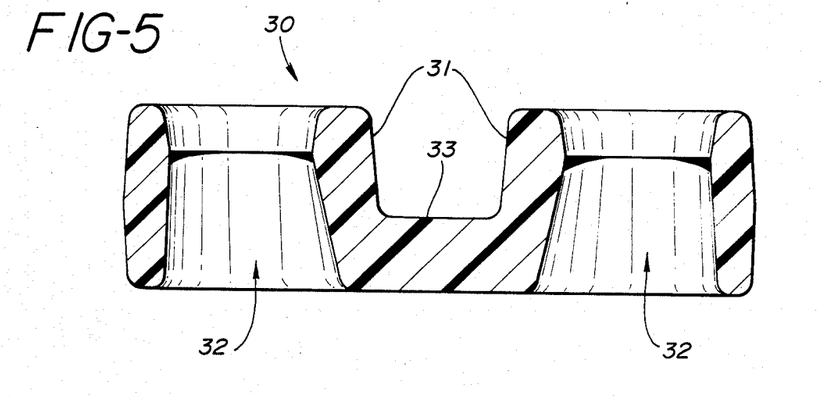
FIG. 5 is a cross-sectional view taken along line 5—5 of FIG. 4.
Figure 6:
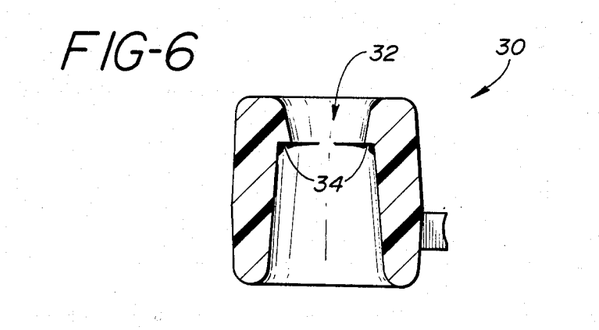
FIG. 6 is another cross-sectional view taken along line 6—6 of FIG. 4.

Individual receivers are more clearly depicted in FIGS. 4, 5, and 6. Each receiver 30 comprises a body member 31 and disposed in that body member are two openings 32. The center point of each opening coincides or is spaced from the center point of the other opening by the distance between the center lines of the staple legs. As shown in FIG. 5, it is preferred that the center portion 33 of the body be depressed to allow the fastening system to be used with a broader range of tissue thickness. By shaping the openings as shown, that is in an oval manner, the alignment of the staple legs and the openings is not as critical and if the staple legs tend to bend or get off line slightly when penetrating the tissue, they still will engage the oval openings of the receiver. As shown in FIG. 6, immediately below the opening is a ledge 34 and once the staple leg penetrates the tissue the appropriate ledges on the staple legs will be engaged by the ledge in the opening to lock the staple leg therewith. If thick tissue is being joined, the ledges closest to the tip of the leg of the staple engage the ledge in the opening; whereas, if thinner tissue is being joined, the ledges on the staple leg disposed furtherest from the staple leg engage the ledge in the opening of the receiver.

Figure 7:
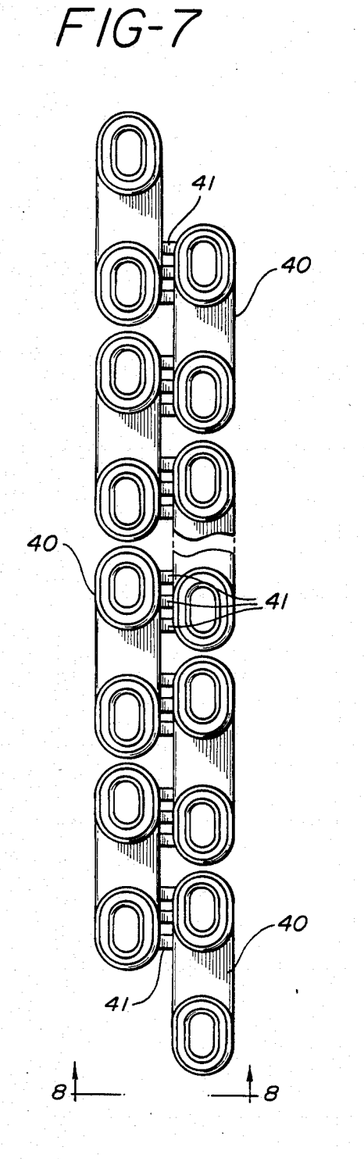
FIG. 7 is a top view of a plurality of connected receivers of the fastening system of the present invention.
Figure 8:
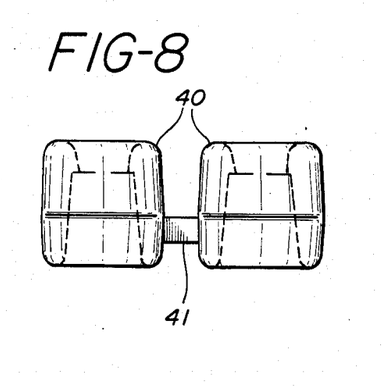
FIG. 8 is an end view of the two lines of receivers shown in FIG. 7.

As shown in FIGS. 7 and 8, there are two parallel rows of receivers. Each receiver 40 is connected to at least two adjacent receivers with the exception, of course, of the last receiver at one end of each row. Each connection is accomplished by a plurality of parallel linkages 41. As previously mentioned, it is important that each receiver by connected to at least two adjacent receivers and that each connection be a plural connection. This configuration of connections provides the desired integrity, rigidity and flexibility in the receiver to provide excellent hemostatis with our improved fastening system, especially when the system is made from absorbable polymer.

Figure 9:
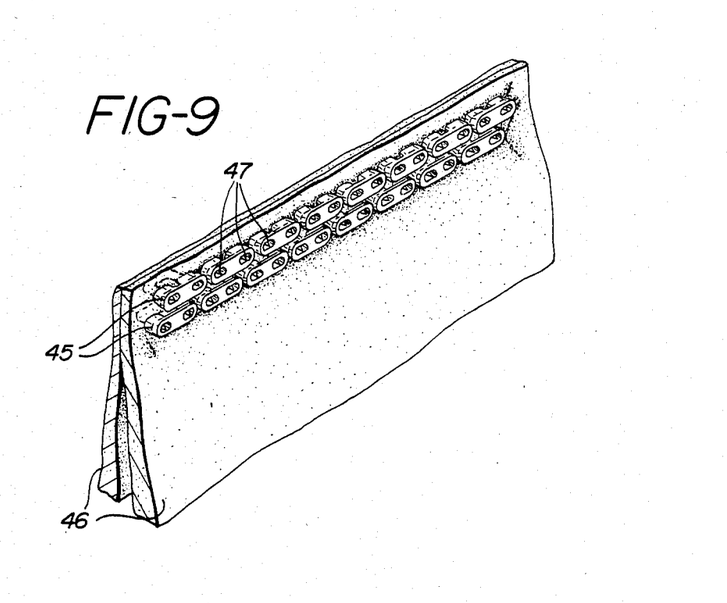
FIG. 9 is a perspective view of the new fattening system in place joining tissue.

Referring to FIG. 9 there is shown the parallel rows of receivers 45 in place on one side of the tissue 46 being joined. The legs 47 of the staples on the opposite side of the tissue are locked in the openings of the receivers to hold the tissue together.

As shown in FIG. 8, the linkages are disposed from the top of the receivers and are closer to the bottom f the receivers to allow for excess tissue to overlap and fill up that area if desired.

Figure 10:
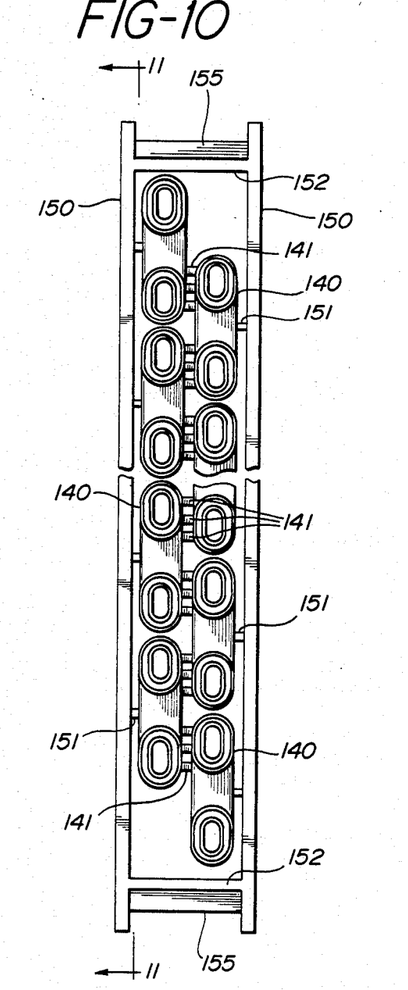
FIG. 10 is a top view of a second preferred embodiment of a receiver used in the fastening system of the present invention.
Figure 11:
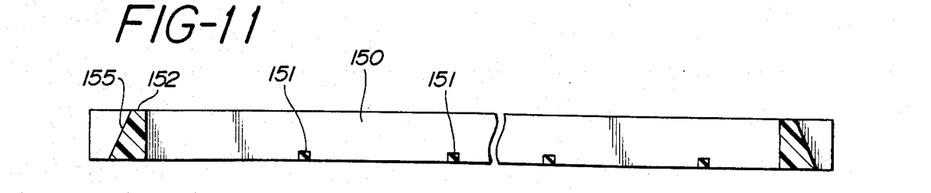
FIG. 11 is a cross sectional view taken along lines 11—11 of FIG. 10.
Figure 12:
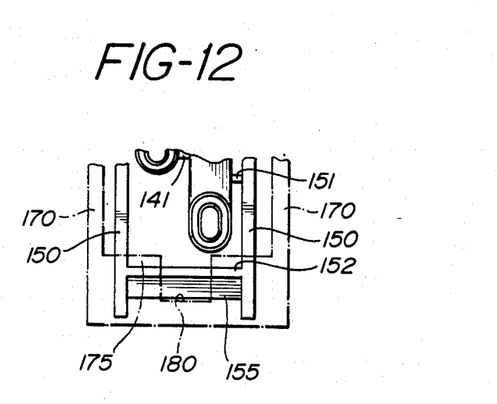
FIG. 12 is a top view of a receiver used in the second preferred embodiment of the fastening system of the present invention seated beneath a receiver containing clamp for staple receiving purposes.

A second preferred embodiment of the receivers of the Present invention is seen in FIGS. 10, 11 and 12. Receivers 140 are connected by parallel linkages 141 as in the first preferred embodiment of the present invention. These receivers are also connected to cassette 150 by means of break-off tabs or linkages 151. The linkages 151 are smaller in height than the height of cassette 150, as seen in FIG. 11. Generally the linkages 151 have a cross section of 0.005". The cassette 150 is joined by two cross members 152, both of which terminate in ramps 155, as seen in FIGS. 10 and 11.

In operation, the retainers 140 attached to the cassette 150 are placed within a staple forming bracket 170, as seen in FIG. 12. Included in this staple forming bracket is a cross member 175, which fits over the cassette 150 as well as the cross member 152 and the ramp 155. The cross member 175 contains a notch 180, specifically formed for break off of the cassette 150. In operation, the break-off linkages 151 along with the cassette 150 are placed flush against the base of the stapler. When the staples are driven into the linkages 140, a pusher bar not shown passes down through the notch 180, and onto the ramp 155. This creates both a downward and a lateral force on the cassette 150. Because the base of the cassette 150 is not able to move downwardly, it is forced to move laterally, resulting in the shearing of linkages 151. This shearing results in the staples remaining clamped to the retainers 140 while the cassette 150 remains within the stapler.

Figure 13:
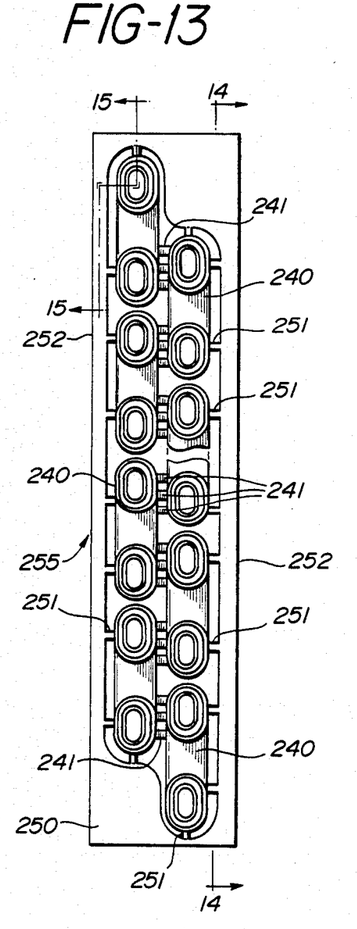
FIG. 13 is a top view of a third preferred embodiment of a receiver used in the fastening system of the present invention.
Figure 14:
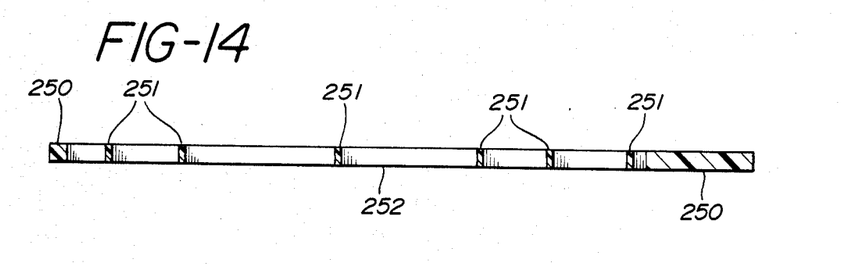
FIG. 14 is a cross sectional view taken along lines 14—14 of FIG. 13.
Figure 15:
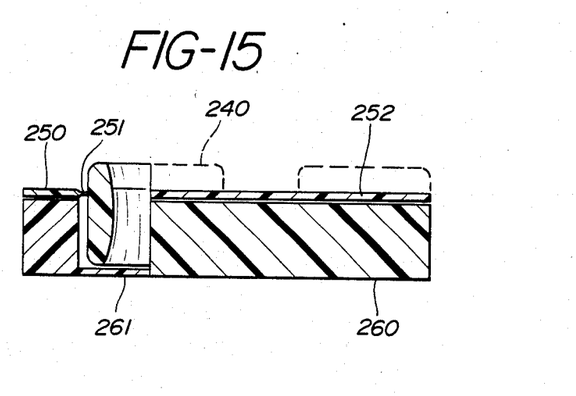
FIG. 15 is a cross sectional view taken along lines 15—15 of FIG. 13.

A third preferred embodiment of the present invention is demonstrated in FIGS. 13, 14 and 15. As seen in FIG. 13, there are receivers 240 identical in shape and function to the receivers 40, 140 of the two previously described embodiments. These receivers 240 are arranged in parallel and are connected by means of a plurality of parallel linkages 241. The receivers 240 are also connected on their outer edges to the rails 252 of a ribbon cassette 255 by means of connecting linkages 251. Each of the rails 252 is connected to one another by means of a connecting plate 250.

When the ribbon cassette 255 containing the receivers 240 is placed in a forming tray 260, the rails 252 of the cassette 255 are seated such that the bottom of the retainers 240 does not touch the base 261 of the forming tray 260. When staples are driven into the receivers 240, they are deflected in the direction of the base of the receivers 240. At this point, the linkages 251 snap from the connecting plate 250 and the rails 252 such that the staples when seated in the receivers 240 are removable from the ribbon cassette 255. This occurs because the diameter of the linkages 251 are formed far smaller than the height of the rails 252 or the connecting plate 250 of the ribbon cassette 255. Generally, the rails 252 have a diameter of about 0.020" and the linkage 257 will have a diameter of 0.005". In this way, after breaking from the linkages 251, the retainers 240 wit their staples may be used apart from the ribbon cassette 255.

Figure 16:
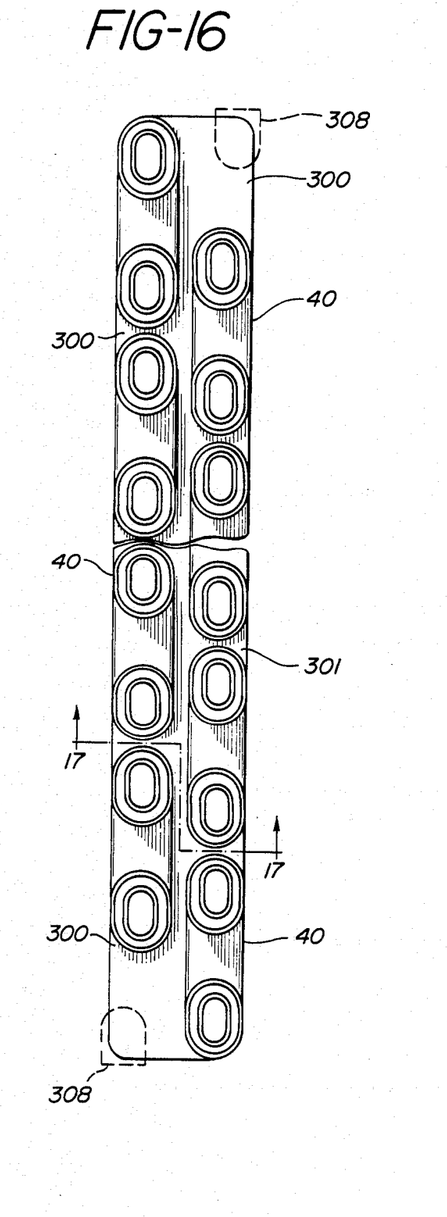
FIG. 16 is a top view of a plurality of connected receivers of another embodiment of the fastening system of the present invention.

Referring to FIGS. 16-21, further embodiments of the present invention are shown. In FIG. 16, the individual receivers 40 of two rows of receivers are interconnected by a continuous thin layer or web 300 of the plastic material of which the receivers are formed. The web 300 is formed between the two rows of receivers, and extends to the outer longitudinal sides of the rows between opposing receiver ends, as shown at 301. The web extends longitudinally from the top of the uppermost receiver to the bottom of the lowermost receiver. These extensions of the web adjacent the uppermost and lower most receivers provide a means for retaining the array of joined receivers in a stapling instrument. For example, the instrument may include retaining brackets 308 at the top and bottom of the array as illustrated in phantom in the drawing Figure. These brackets help retain the web-connected receivers in the instrument. When the receivers are engaged by staples during a fastening procedure, thereby attaching the receivers to tissue, the receivers will be pulled away from the instrument as the flexible web extensions bend out from behind the brackets.

Figure 17:
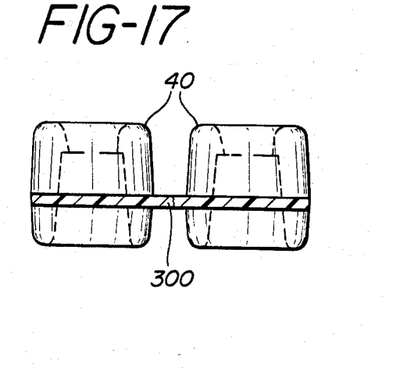
FIG. 17 is a cross-sectional view of the embodiment of FIG. 16.
Figure 18:
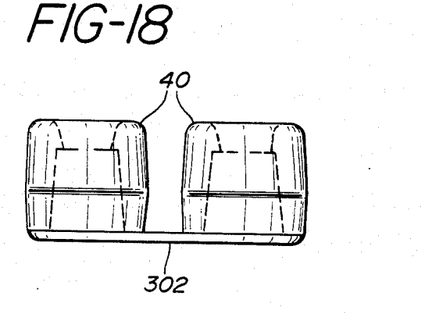
FIGS. 18 and 19 are alternate embodiments of the fastening system of FIG. 16.
Figure 19:
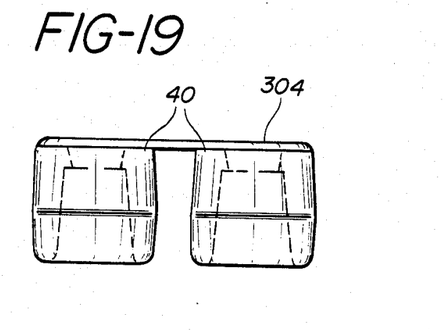

In the embodiments of FIGS. 16 and 17, the web 300 is centrally located, at approximately the level of the linkages 41 in FIG. 7. The web is thin, having a thickness in the range of 0.005 to 0.010 inches, the exact thickness being determined by molding considerations. Instead of locating the web midway along the receivers, the web may alternatively extend along the bottom or top of the array of receivers, as shown by webs 302 and 304 of FIGS. 18 and 19. The thin web advantageously allows the joined array of receivers to flex and bend in the body, permitting the array to contour and follow the shape of the tissue being joined. The thin web of absorbable polymeric material will also absorb rather rapidly in the body, leaving the connected receivers and staples free to follow the contours of the healing tissue.

Figure 20:
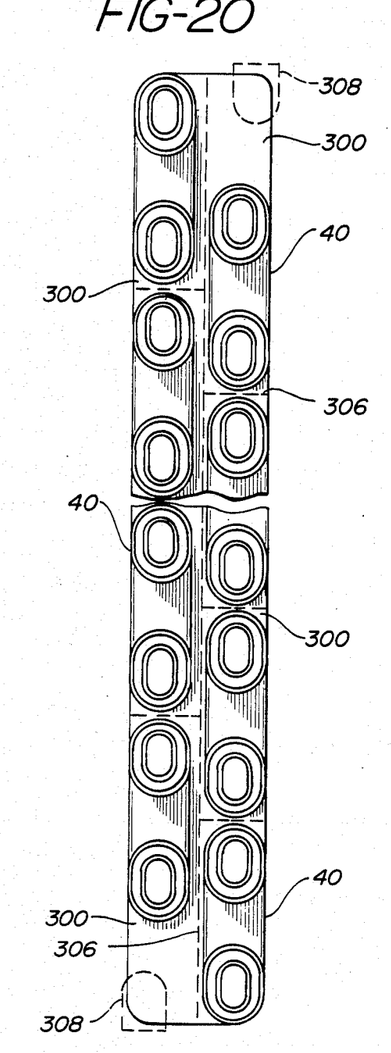
FIGS. 20 and 21 are a modification of the embodiment of FIG. 16 affording an ease of separation of the connected receivers.
Figure 21:
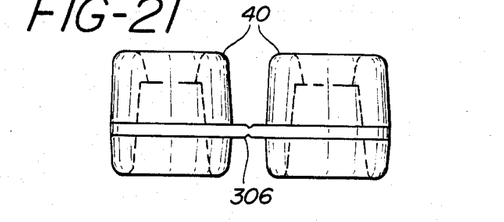

FIG. 20 shows a modification of the joined receivers of FIG. 16 in which break lines 306 are indented into the web 300 between the receivers 40. The break lines extend longitudinally between the two rows and outward between individual receivers. The break lines 306 are formed by pressing or notching the web with a sharp instrument, either from above, below, or both. The notching of the web at the break lines permits the array to be broken along the lines when it is desired to use less than all of the receivers in the array. For instance, this would permit a normal 66 mm array to be shortened to 50 mm in length when lines of receivers of that length are required for a particular surgical procedure.

Figure 22:
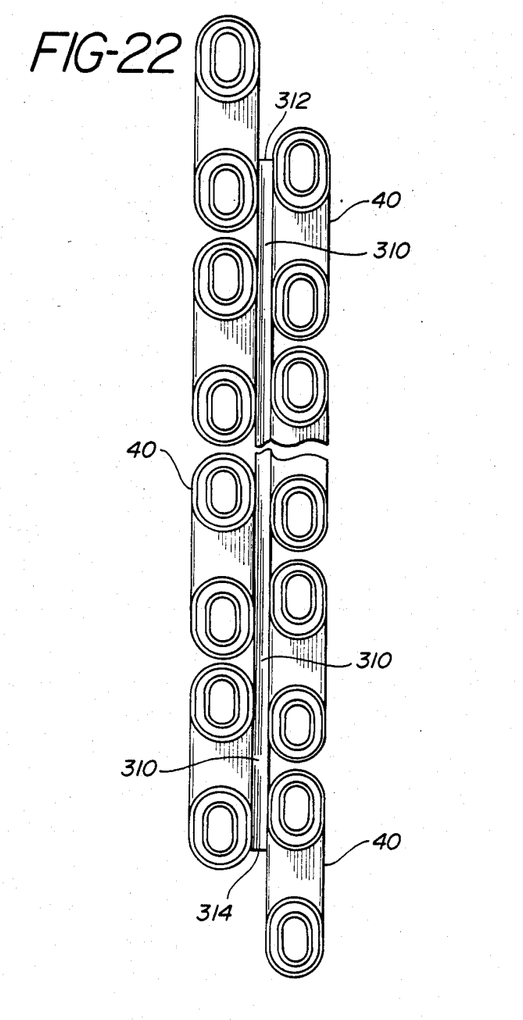
FIG. 22 is a top view of a further embodiment of the fastening system of the present invention.
Figure 23:
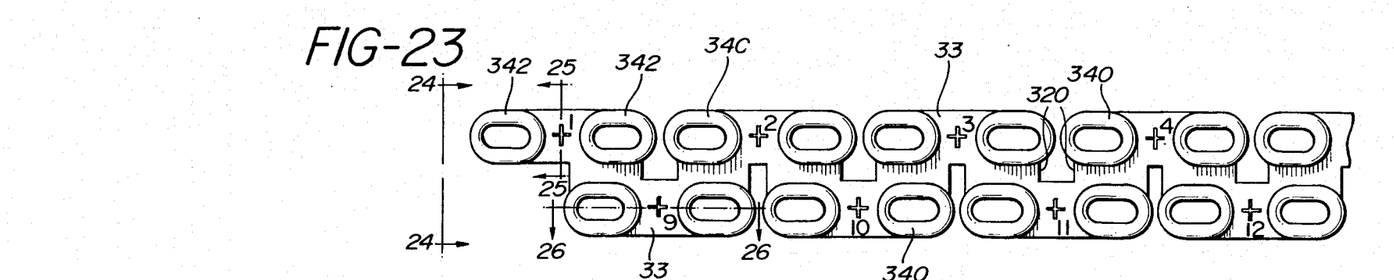

FIG. 22 illustrates another embodiment of the present invention, in which the two rows of receivers are joined by a bar or web 310 extending between the two rows. This configuration would look similar to FIG. 8 when viewed from the end of the array. This embodiment provides all of the advantages of the FIG. 16 embodiment, with improved degrees of flexibility. Individual ones of the joined receivers 40 can bend rotationally, as they are free to pivot around their inner longitudinal jointures to the central bar or web 310. Since the individual receivers are not connected end-to-end as in the previous embodiment, there is no restraint on such pivoting which end-to-end connections would impose. The array of joined receivers can be easily shortened by breaking the central bar or web 310 at a desired point of the array. As before, the thickness of the bar or web is determined by molding considerations and the desired rapidity of web absorption, and the central web or bar 310 can be located at any level between the tops and bottoms of the receivers.

Figure 24:
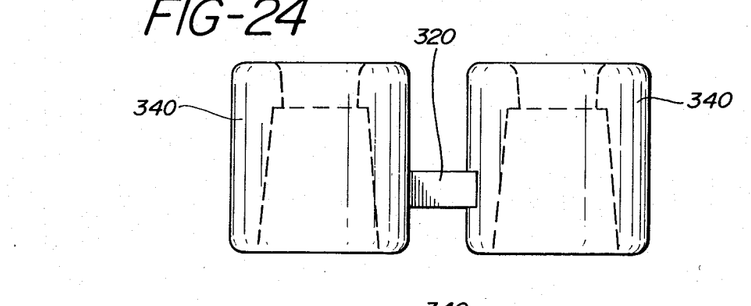
Figure 25:
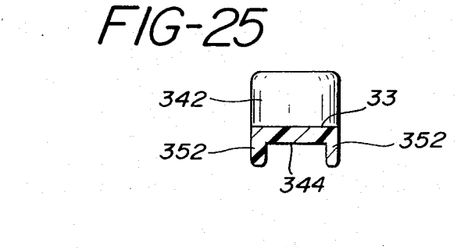
Figure 26:
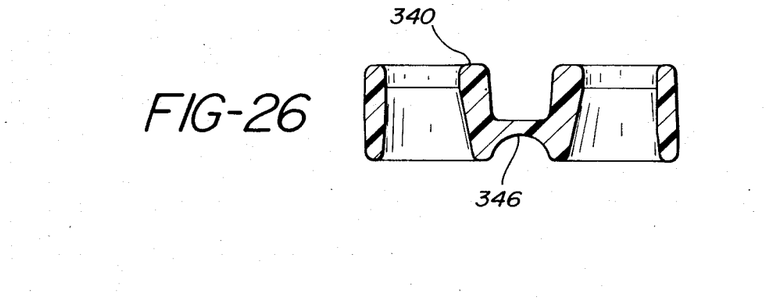
Figure 27:
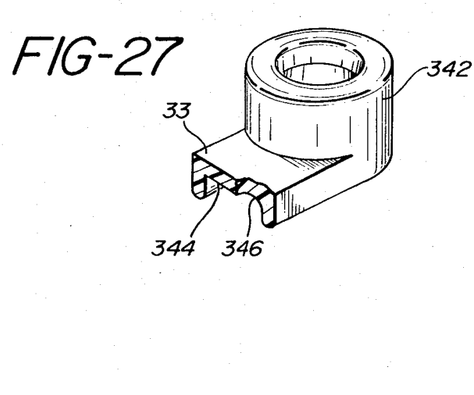

FIGS. 23-27 illustrate yet another embodiment of the present invention, in which the central region of each receiver is thinned for rapid absorption and is channeled to provide stiffness during the stapling procedure. The two rows of receivers 340 are interconnected by regions 320 of absorbable material. In this embodiment the upper surfaces of the regions 320 are coplanar with the upper surfaces of the regions 33 between the apertured ends 342 of each receiver. In this embodiment the interconnecting regions 320 have a thickness of approximately 0.013 to 0.015 inches. An end view of the array of receivers showing the interconnecting region 320 is shown in FIG. 24. The regions 33 between each apertured receiver end 342 are of the same thickness. To provide stiffness to the receivers, each region 33 is channeled in two dimensions. Across the center of each region 33 between the apertured ends the region is angularly channeled, as shown at 344 in FIG. 25. The downwardly depending sides 352 of each channeled region are slightly thinner than the horizontal center of the channeled region, being approximatley 0.010 inches in thickness. In the longitudinal direction of each receiver, the region 33 is arcuately channeled, as shown at 346 in FIG. 26. The radius of curvature of the arcuate channel 346 in this embodiment is approximately 0.025 inches. It has been found that the angular channeling 344 alone causes the central region 33 of the receiver to be three times stiffer than the interconnecting regions 320. When the arcuate channeling is added, a further improvement in receiver stiffness is afforded. Thus, the two rows of receivers are relatively flexible along their longitudinally interconnected center, but the individual receivers are much stiffer between the apertured ends, despite being made of material of the same thickness. In FIG. 27, both the cross-wise angular channeling 344 and the arcuate longitudinal channeling 346 of an individual receiver are illustrated.

The fastening systems of the present invention may be made from any of the absorbable polymeric materials. Examples of suitable polymers are the polymers and copolymers of lactide, glycolide, dioxanone, and the like.

Having now described the invention, it will be readily apparent to those skilled in the art that there are many variations and modifications which may be made to the invention without departing from the spirit and scope thereof.

What is claimed is:

1. In a surgical fastening system for joining tissue, said system comprising a plurality of parallel rows of staples and a plurality of parallel rows of receivers, each of said staples comprising a pair of legs, said legs being joined at one end thereof by a linking member, the opposite end of each leg being adapted to penetrate tissue so the linking member lies adjacent the tissue penetrated by said legs, each receiver having a body portion and a plurality of openings disposed in said body portion, said openings being located so as to engage the legs of the staple after said legs have penetrated the tissue so that the receiver lies on the opposite side of the tissue to be joined, means on said legs and on said receivers for interlocking the staple and the receiver together; the improvement comprising each receiver being connected to at least two receivers in an adjacent row with each connection comprising a plurality of parallel linkages between receivers, said linkages being flexible and sufficiently strong to maintain the receivers connected during both the application of the fastening system when joining the tissue and the use of the fastening system to hold the tissue until such tissue has healed.

2. A surgical fastening system according to claim 1 wherein the openings in the receiver each have an oval shape.

3. A surgical fastening system according to claim 1 wherein each connection between receivers comprises three parallel linkages.

4. A system for holding surgical staples comprising receivers having a body portion and plurality of openings in said portion, said receivers held in parallel rows by means of a plurality of linkages attached to a row maintaining cassette on the outside of said parallel rows, said row maintaining cassette comprising a pair of parallel rails connected by a pair of parallel ramps, said ramps configured for emplacement beneath a receiver maintaining mold.

5. The system of claim 4 wherein said ramps are capable of receiving a breaking force, said force causing motion of said row maintaining cassette with respect to said receivers, said force causing said plurality of linkages to break away from said receivers.

6. The system of claim 5 wherein each receiver is connected to said row maintaining cassette by at least one of said linkages.

7. The system of claim 6 wherein said linkages have a cross sectional diameter of about 0.005".

8. The system of claim 4 wherein said openings in the receiver each have an oval shape.

9. A system for holding surgical staples comprising receivers having a body portion and a plurality of openings in said body portion, said receivers held in parallel rows by means of a plurality of linkages attached to a ribbon cassette outside said parallel rows, said ribbon cassette comprising a flat plate adapted for emplacement on a platform, said ribbon cassette causing said receivers to have a clearance from the base of said platform such that when surgical staples are driven into said receivers, forces imparted on said receivers from said surgical staples cause said linkages to break, separating said ribbon cassette from said receivers.

10. The system of claim 9 wherein each receiver is connected to said ribbon cassette by means of at least two said linkages.

11. The system of claim 10 wherein said linkages have a cross sectional diameter of about 0.005".

12. The system of claim 9 wherein said openings in said receiver each have an oval shape.

13. In a surgical fastening system for joining tissue, said system comprising a plurality of parallel rows of staples and a plurality of parallel rows of receivers, each of said staples comprising a pair of legs, said legs being joined at one end thereof by a linking member, the opposite end of each leg being adapted to penetrate tissue so the linking member lies adjacent the tissue penetrated by said legs, each receiver having a body portion and a plurality of openings disposed in said body portion, said openings being located so as to engage the legs of the staple after said legs have penetrated the tissue so that the receiver lies o the opposite side of the tissue to be joined, means on said legs and on said receivers for interlocking the staple and the receiver together; the improvement comprising each receiver being connected to a least two receivers in an adjacent row by means of a web extending between said rows, wherein each of said receivers are attached to the web at and along longitudinally opposing sides.

14. A surgical fastening system according to claim 13, wherein said web further extends between the opposing ends of receivers in each row, terminating at the line of the outer longitudinal sides of the receivers of each row.

15. A surgical fastening system according to claim 13, wherein said web is centered at a level between the planes of the tops and bottom of the receiver.

16. A surgical fastening system according to claim 13, wherein said web is located at a level which is at the bottom of said receivers.

17. A surgical fastening system according to claim 13, wherein said web is located at a level which is at the tops of said receivers.

18. A surgical fastening system according to claim 14, wherein said web is indented between ones of said receivers to allow said connected receivers to be separated.

19. A surgical fastening system according to claim 13, wherein said web extends laterally between said rows to the respective lines of the opposing longitudinal sides of said receivers.

20. A surgical fastening system according to claim 13, wherein the cross-section of the central body region of each receiver comprises a channel shape.

21. A surgical fastening system according to claim 13, wherein the cross-section of the central body region of each receiver comprises an angular channel in one dimension, and an arcuate channel in a second dimension.

22. A surgical fastening system according to claim 20, wherein the web between said rows is notched in a lateral direction extending toward the center of the region between the rows from opposing ends of ones of said receivers.

* * * * *